United States Patent [19]
White et al.

[11] Patent Number: 5,484,705
[45] Date of Patent: Jan. 16, 1996

[54] METHOD FOR QUANTIFYING LIPOPOLYSACCHARIDE BINDING PROTEIN

[75] Inventors: Mark L. White, Sonoma; Stephen F. Carroll, Walnut Creek; Jeremy K. Ma, San Ramon, all of Calif.

[73] Assignee: XOMA Corporation, Berkeley, Calif.

[21] Appl. No.: 186,811

[22] Filed: Jan. 24, 1994

[51] Int. Cl.$^6$ ............... G01N 33/566; G01N 33/569; C12Q 1/00
[52] U.S. Cl. ............. 435/7.32; 435/7.5; 435/7.92; 435/7.95; 436/501; 436/811
[58] Field of Search ............. 435/7.32, 7.9, 435/7.92–7.95, 7.5; 436/501, 811

[56] References Cited

U.S. PATENT DOCUMENTS

5,245,013 9/1993 Ulevitch et al. .................. 530/380

FOREIGN PATENT DOCUMENTS

WO91/01639 2/1991 WIPO.
WO93/06228 4/1993 WIPO.
WO94/21280 9/1994 WIPO.

OTHER PUBLICATIONS

Dofferhoff, et al., "Tumor necrosis factor (cachectin) and other cykotines in septic shock: a review of the literature," *Netherlands Journal of Medicine*, 39:45–62 (1991).
Elsbach et al., "Separation and Purification of a Potent Bactericidal/Permeability–Increasing Protein and a Closely Associated Phospholipase A$_2$ from Rabbit Polymorphonuclear Leukocytes," *J. Biol. Chem.*,254:11000–11009 (1979).
Erwin, et al., "Plasma Lippopolysaccharide–Deacylating Activity (Acyloxyacl Hydrolase) Increase After Lippopolysaccharide Administration to Rabbits," *Laboratory Investigation*, 65(2):138–144 (1991).
Gallay, et al., "Purification and Characterization of Murine Lipopolysaccharide–Binding Protein," *Infection and Immunity*, 61(2):378–383, (Feb., 1993).
Gazzano–Santoro et al., "High–Affinity Binding of the Bactericidal/Permeability–Increasing Protein and a Recombinant Amino–Terminal Fragment to the Lipid A Region of Lipopolysaccharide," *Infection and Immunity*, 60(11):4754–4761 (1992).
Geller, et al., "Induction of Hepatocyte Lipopolysaccharide Binding Protein in Models of Sepsis and the Acute–Phase Response," *Arch. Surg.* 128:22–28, (Jan., 1993).
Leturcq et al., "Generation of Monoclonal Antibodies to Human LBP and their Use in the Detection of LBP Protein in Serum," *J. Cell. Biochem.*, 16C:161 (1992).
Marra, et al., "The Role of Bactericidal/Permeability–Increasing Protein as a Natural Inhibitor of Bacterial Endotoxin," *J. Immunol.*, 148(2):532–537 (Jan. 15, 1992).
Pereira et al., "Quantitation of a Cationic Antimicrobial Granule Protein of Human Polymorphonuclear Leukocytes by ELISA," *J. Immunol. Methods*, 117:115–120 (1989).
Pesce et al., "Cationic Antigens—Problems Associated with Measurement by ELISA," *J. Immunol. Methods*, 87:21–27 (1986).
Schindler, et al., "Plasma levels of bactericidal/permeability–increasing protein (BPI) and lippopolysaccharide–binding protein (LBP) during hemodialysis," *Clinical Nephrology*, 40(6):346–351 (1993).
Schumann, et al., "Structure and Function of Lippopolysaccharide Binding Protein," *Science*, 249:1429–1433 (Sep. 21, 1990).
Spitznagel, et al., "Antibiotic Proteins of Human Neutrophils," *J. Clin. Invest.*, 86:1381–1386 (1990).
Taber, et al., *"Taber's Cyclopedic Medical Dictionary,"* Philadelphia: F. A. Davis Company, p. 545 (1985).
von der Mohien, et al., "Bactericidal Permeability Increasing Protein Levels Predict Survival in Patients with Gram–Negative Sepsis," Abstract presented at 13th International Symposium on Intensive Care and Emergency Medicine, (Brussels, Belgium) (1993).
Weiss, et al., "Cellular and Subcellular Localization of the Bactericidal/Permeability–Increasing Protein of Neutrophils," *Blood*, 69(2):652–659 (1987).
Weiss, et al., "Human Bactericidal/Permeability–Increasing Protein and a Recombinant NH$_2$–Terminal Fragment Cause Killing of Serum–Resistant Gram–Negative Bacteria in Whole Blood and Inhibit Tumor Necrosis Factor Release Induced by the Bacteria," *J. Clin. Invest.*, 90:1122–1130 (Sep., 1992).
Weiss, et al., "Purification and Characterization of a Potent Bactericidal and Membrane Active Protein from the Granules of Human Polymorphonuclear Leukocytes," *J. Biol. Chem.*, 253(8):2664–2672 (1978).
Wright, et al., "CD14, a Receptor for Complexes of Lipopolysaccharide (LPS) and LPS Binding Protein," *Science*, 249:1431–1433 (Sep. 21, 1990).
Ulevitch, Presentation at the American Society of Microbiology General Meeting in Atlanta, Ga. (May 16–21, 1993) (Session 13 Abstract 564).
Tobias et al., "Lipopolysaccharide Binding Protein", *J. Cell. Biochem.*, 16 C:151 (Abstract (CB006) (1992).
Ballou et al., "Laboratory Evaluation of Inflammation," *Textbook of Rheumatolgy*, vol. 1, Ch. 40, pp. 671–679 (1993).
Baumann et al., "The acute phase response," *Immunology Today*, vol. 15, No. 2, pp. 74–80 (1994).
Grube et al., "Lipopolysaccharide Binding Protein Expression in Primary Human Hepatocytes and HepG2 Hepatoma Cells*," *J. Biol. Chem.*, vol. 269, No. 11, pp. 8477–8482 (1994).
Raynes, "Carbohydrate Binding Proteins and Immune Responses," Biochemical Immunology Group/Glycobiology Group Joint Colloquium Organized by G. B. Wisdom and M. I. Halliday (The Queen's University, Belfast) and Edited by G. B. Wisdom. 648th Meeting held at The Queen's University, Belfast, 14–17 Sep. 1993, *Biochemical Society Transactions*, vol. 22, pp. 69–74 (1994).

*Primary Examiner*—Toni R. Scheiner
*Assistant Examiner*—Patricia A. Duffy
*Attorney, Agent, or Firm*—Marshall, O'Toole, Gerstein, Murray & Borun

[57] ABSTRACT

The present invention provides a method for quantifying the presence of extracellular LBP in body fluids including blood in a subject comprising conducting an LBP immunoassay on plasma obtained from said subject.

2 Claims, 4 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 1443 base pairs
    ( B ) TYPE: nucleic acid
    ( C ) STRANDEDNESS: single
    ( D ) TOPOLOGY: linear ( i i ) MOLECULE TYPE: DNA ( i x ) FEATURE:
    ( A ) NAME/KEY: CDS
    ( B ) LOCATION: 1..1443

( i x ) FEATURE:
    ( A ) NAME/KEY: mat_peptide
    ( B ) LOCATION: 76..1443

( i x ) FEATURE:
    ( A ) NAME/KEY: misc_feature
    ( D ) OTHER INFORMATION: "rLBP"

( x i ) SEQUENCE DESCRIPTION: SEQ ID NO:1:

| ATG | GGG | GCC | TTG | GCC | AGA | GCC | CTG | CCG | TCC | ATA | CTG | CTG | GCA | TTG | CTG | 48 |
| Met | Gly | Ala | Leu | Ala | Arg | Ala | Leu | Pro | Ser | Ile | Leu | Leu | Ala | Leu | Leu | |
| -25 | | | | -20 | | | | | -15 | | | | | | -10 | |

| CTT | ACG | TCC | ACC | CCA | GAG | GCT | CTG | GGT | GCC | AAC | CCC | GGC | TTG | GTC | GCC | 96 |
| Leu | Thr | Ser | Thr | Pro | Glu | Ala | Leu | Gly | Ala | Asn | Pro | Gly | Leu | Val | Ala | |
| | | | | -5 | | | | | 1 | | | | | 5 | | |

| AGG | ATC | ACC | GAC | AAG | GGA | CTG | CAG | TAT | GCG | GCC | CAG | GAG | GGG | CTA | TTG | 144 |
| Arg | Ile | Thr | Asp | Lys | Gly | Leu | Gln | Tyr | Ala | Ala | Gln | Glu | Gly | Leu | Leu | |
| | | 10 | | | | | | 15 | | | | | 20 | | | |

| GCT | CTG | CAG | AGT | GAG | CTG | CTC | AGG | ATC | ACG | CTG | CCT | GAC | TTC | ACC | GGG | 192 |
| Ala | Leu | Gln | Ser | Glu | Leu | Leu | Arg | Ile | Thr | Leu | Pro | Asp | Phe | Thr | Gly | |
| | | 25 | | | | 30 | | | | | 35 | | | | | |

| GAC | TTG | AGG | ATC | CCC | CAC | GTC | GGC | CGT | GGG | CGC | TAT | GAG | TTC | CAC | AGC | 240 |
| Asp | Leu | Arg | Ile | Pro | His | Val | Gly | Arg | Gly | Arg | Tyr | Glu | Phe | His | Ser | |
| 40 | | | | | 45 | | | | | 50 | | | | | 55 | |

| CTG | AAC | ATC | CAC | AGC | TGT | GAG | CTG | CTT | CAC | TCT | GCG | CTG | AGG | CCT | GTC | 288 |
| Leu | Asn | Ile | His | Ser | Cys | Glu | Leu | Leu | His | Ser | Ala | Leu | Arg | Pro | Val | |
| | | | | 60 | | | | | 65 | | | | | 70 | | |

| CCT | GGC | CAG | GGC | CTG | AGT | CTC | AGC | ATC | TCC | GAC | TCC | TCC | ATC | CGG | GTC | 336 |
| Pro | Gly | Gln | Gly | Leu | Ser | Leu | Ser | Ile | Ser | Asp | Ser | Ser | Ile | Arg | Val | |
| | | | 75 | | | | | 80 | | | | | 85 | | | |

| CAG | GGC | AGG | TGG | AAG | GTG | CGC | AAG | TCA | TTC | TTC | AAA | CTA | CAG | GGC | TCC | 384 |
| Gln | Gly | Arg | Trp | Lys | Val | Arg | Lys | Ser | Phe | Phe | Lys | Leu | Gln | Gly | Ser | |
| | | 90 | | | | | 95 | | | | | 100 | | | | |

| TTT | GAT | GTC | AGT | GTC | AAG | GGC | ATC | AGC | ATT | TCG | GTC | AAC | CTC | CTG | TTG | 432 |
| Phe | Asp | Val | Ser | Val | Lys | Gly | Ile | Ser | Ile | Ser | Val | Asn | Leu | Leu | Leu | |
| | 105 | | | | | 110 | | | | | 115 | | | | | |

| GGC | AGC | GAG | TCC | TCC | GGG | AGG | CCC | ACA | GTT | ACT | GCC | TCC | AGC | TGC | AGC | 480 |
| Gly | Ser | Glu | Ser | Ser | Gly | Arg | Pro | Thr | Val | Thr | Ala | Ser | Ser | Cys | Ser | |
| 120 | | | | | 125 | | | | | 130 | | | | | 135 | |

| AGT | GAC | ATC | GCT | GAC | GTG | GAG | GTG | GAC | ATG | TCG | GGA | GAC | TTG | GGG | TGG | 528 |
| Ser | Asp | Ile | Ala | Asp | Val | Glu | Val | Asp | Met | Ser | Gly | Asp | Leu | Gly | Trp | |
| | | | | 140 | | | | | 145 | | | | | 150 | | |

| CTG | TTG | AAC | CTC | TTC | CAC | AAC | CAG | ATT | GAG | TCC | AAG | TTC | CAG | AAA | GTA | 576 |
| Leu | Leu | Asn | Leu | Phe | His | Asn | Gln | Ile | Glu | Ser | Lys | Phe | Gln | Lys | Val | |
| | | | 155 | | | | | 160 | | | | | 165 | | | |

```
CTG GAG AGC AGG ATT TGC GAA ATG ATC CAG AAA TCG GTG TCC TCC GAT      624
Leu Glu Ser Arg Ile Cys Glu Met Ile Gln Lys Ser Val Ser Ser Asp
        170                 175                 180

CTA CAG CCT TAT CTC CAA ACT CTG CCA GTT ACA ACA GAG ATT GAC AGT      672
Leu Gln Pro Tyr Leu Gln Thr Leu Pro Val Thr Thr Glu Ile Asp Ser
        185                 190                 195

TTC GCC GAC ATT GAT TAT AGC TTA GTG GAA GCC CCT CGG GCA ACA GCC      720
Phe Ala Asp Ile Asp Tyr Ser Leu Val Glu Ala Pro Arg Ala Thr Ala
200                     205                 210                 215

CAG ATG CTG GAG GTG ATG TTT AAG GGT GAA ATC TTT CAT CGT AAC CAC      768
Gln Met Leu Glu Val Met Phe Lys Gly Glu Ile Phe His Arg Asn His
                    220                 225                 230

CGT TCT CCA GTT ACC CTC CTT GCT GCA GTC ATG AGC CTT CCT GAG GAA      816
Arg Ser Pro Val Thr Leu Leu Ala Ala Val Met Ser Leu Pro Glu Glu
            235                 240                 245

CAC AAC AAA ATG GTC TAC TTT GCC ATC TCG GAT TAT GTC TTC AAC ACG      864
His Asn Lys Met Val Tyr Phe Ala Ile Ser Asp Tyr Val Phe Asn Thr
        250                 255                 260

GCC AGC CTG GTT TAT CAT GAG GAA GGA TAT CTG AAC TTC TCC ATC ACA      912
Ala Ser Leu Val Tyr His Glu Glu Gly Tyr Leu Asn Phe Ser Ile Thr
        265                 270                 275

GAT GAG ATG ATA CCG CCT GAC TCT AAT ATC CGA CTG ACC ACC AAG TCC      960
Asp Glu Met Ile Pro Pro Asp Ser Asn Ile Arg Leu Thr Thr Lys Ser
280                     285                 290                 295

TTC CGA CCC TTC GTC CCA CGG TTA GCC AGG CTC TAC CCC AAC ATG AAC     1008
Phe Arg Pro Phe Val Pro Arg Leu Ala Arg Leu Tyr Pro Asn Met Asn
                    300                 305                 310

CTG GAA CTC CAG GGA TCA GTG CCC TCT GCT CCG CTC CTG AAC TTC AGC     1056
Leu Glu Leu Gln Gly Ser Val Pro Ser Ala Pro Leu Leu Asn Phe Ser
            315                 320                 325

CCT GGG AAT CTG TCT GTG GAC CCC TAT ATG GAG ATA GAT GCC TTT GTG     1104
Pro Gly Asn Leu Ser Val Asp Pro Tyr Met Glu Ile Asp Ala Phe Val
        330                 335                 340

CTC CTG CCC AGC TCC AGC AAG GAG CCT GTC TTC CGG CTC AGT GTG GCC     1152
Leu Leu Pro Ser Ser Ser Lys Glu Pro Val Phe Arg Leu Ser Val Ala
        345                 350                 355

ACT AAT GTG TCC GCC ACC TTG ACC TTC AAT ACC AGC AAG ATC ACT GGG     1200
Thr Asn Val Ser Ala Thr Leu Thr Phe Asn Thr Ser Lys Ile Thr Gly
360                 365                 370                 375

TTC CTG AAG CCA GGA AAG GTA AAA GTG GAA CTG AAA GAA TCC AAA GTT     1248
Phe Leu Lys Pro Gly Lys Val Lys Val Glu Leu Lys Glu Ser Lys Val
                380                 385                 390

GGA CTA TTC AAT GCA GAG CTG TTG GAA GCG CTC CTC AAC TAT TAC ATC     1296
Gly Leu Phe Asn Ala Glu Leu Leu Glu Ala Leu Leu Asn Tyr Tyr Ile
            395                 400                 405

CTT AAC ACC TTC TAC CCC AAG TTC AAT GAT AAG TTG GCC GAA GGC TTC     1344
Leu Asn Thr Phe Tyr Pro Lys Phe Asn Asp Lys Leu Ala Glu Gly Phe
        410                 415                 420

CCC CTT CCT CTG CTG AAG CGT GTT CAG CTC TAC GAC CTT GGG CTG CAG     1392
Pro Leu Pro Leu Leu Lys Arg Val Gln Leu Tyr Asp Leu Gly Leu Gln
        425                 430                 435

ATC CAT AAG GAC TTC CTG TTC TTG GGT GCC AAT GTC CAA TAC ATG AGA     1440
Ile His Lys Asp Phe Leu Phe Leu Gly Ala Asn Val Gln Tyr Met Arg
440                 445                 450                 455

GTT                                                                 1443
Val
```

( 2 ) INFORMATION FOR SEQ ID NO:2:

( i ) SEQUENCE CHARACTERISTICS:
  ( A ) LENGTH: 481 amino acids
  ( B ) TYPE: amino acid
  ( D ) TOPOLOGY: linear ( i i ) MOLECULE TYPE: protein ( i x ) FEATURE:
  ( A ) NAME/KEY: misc_feature
  ( D ) OTHER INFORMATION: "rLBP"

( x i ) SEQUENCE DESCRIPTION: SEQ ID NO:2:

| Met | Gly | Ala | Leu | Ala | Arg | Ala | Leu | Pro | Ser | Ile | Leu | Leu | Ala | Leu | Leu |
| -25 | | | | | -20 | | | | -15 | | | | | | -10 |
| Leu | Thr | Ser | Thr | Pro | Glu | Ala | Leu | Gly | Ala | Asn | Pro | Gly | Leu | Val | Ala |
| | | | | -5 | | | | | 1 | | | | 5 | | |
| Arg | Ile | Thr | Asp | Lys | Gly | Leu | Gln | Tyr | Ala | Ala | Gln | Glu | Gly | Leu | Leu |
| | | 10 | | | | | 15 | | | | | | 20 | | |
| Ala | Leu | Gln | Ser | Glu | Leu | Leu | Arg | Ile | Thr | Leu | Pro | Asp | Phe | Thr | Gly |
| | 25 | | | | | 30 | | | | | 35 | | | | |
| Asp | Leu | Arg | Ile | Pro | His | Val | Gly | Arg | Gly | Arg | Tyr | Glu | Phe | His | Ser |
| 40 | | | | | 45 | | | | | 50 | | | | | 55 |
| Leu | Asn | Ile | His | Ser | Cys | Glu | Leu | Leu | His | Ser | Ala | Leu | Arg | Pro | Val |
| | | | | 60 | | | | | 65 | | | | | 70 | |
| Pro | Gly | Gln | Gly | Leu | Ser | Leu | Ser | Ile | Ser | Asp | Ser | Ser | Ile | Arg | Val |
| | | | 75 | | | | | 80 | | | | | 85 | | |
| Gln | Gly | Arg | Trp | Lys | Val | Arg | Lys | Ser | Phe | Phe | Lys | Leu | Gln | Gly | Ser |
| | | | 90 | | | | | 95 | | | | | 100 | | |
| Phe | Asp | Val | Ser | Val | Lys | Gly | Ile | Ser | Ile | Ser | Val | Asn | Leu | Leu | Leu |
| | 105 | | | | | | 110 | | | | | 115 | | | |
| Gly | Ser | Glu | Ser | Ser | Gly | Arg | Pro | Thr | Val | Thr | Ala | Ser | Ser | Cys | Ser |
| 120 | | | | | | 125 | | | | | 130 | | | | 135 |
| Ser | Asp | Ile | Ala | Asp | Val | Glu | Val | Asp | Met | Ser | Gly | Asp | Leu | Gly | Trp |
| | | | | 140 | | | | | 145 | | | | | | 150 |
| Leu | Leu | Asn | Leu | Phe | His | Asn | Gln | Ile | Glu | Ser | Lys | Phe | Gln | Lys | Val |
| | | | 155 | | | | | 160 | | | | | 165 | | |
| Leu | Glu | Ser | Arg | Ile | Cys | Glu | Met | Ile | Gln | Lys | Ser | Val | Ser | Ser | Asp |
| | | | 170 | | | | | 175 | | | | | 180 | | |
| Leu | Gln | Pro | Tyr | Leu | Gln | Thr | Leu | Pro | Val | Thr | Thr | Glu | Ile | Asp | Ser |
| | 185 | | | | | 190 | | | | | 195 | | | | |
| Phe | Ala | Asp | Ile | Asp | Tyr | Ser | Leu | Val | Glu | Ala | Pro | Arg | Ala | Thr | Ala |
| 200 | | | | | 205 | | | | | 210 | | | | | 215 |
| Gln | Met | Leu | Glu | Val | Met | Phe | Lys | Gly | Glu | Ile | Phe | His | Arg | Asn | His |
| | | | | 220 | | | | | 225 | | | | | 230 | |
| Arg | Ser | Pro | Val | Thr | Leu | Leu | Ala | Ala | Val | Met | Ser | Leu | Pro | Glu | Glu |
| | | | 235 | | | | | 240 | | | | | 245 | | |
| His | Asn | Lys | Met | Val | Tyr | Phe | Ala | Ile | Ser | Asp | Tyr | Val | Phe | Asn | Thr |
| | | 250 | | | | | 255 | | | | | 260 | | | |
| Ala | Ser | Leu | Val | Tyr | His | Glu | Glu | Gly | Tyr | Leu | Asn | Phe | Ser | Ile | Thr |
| | 265 | | | | | 270 | | | | | 275 | | | | |
| Asp | Glu | Met | Ile | Pro | Pro | Asp | Ser | Asn | Ile | Arg | Leu | Thr | Thr | Lys | Ser |
| 280 | | | | | 285 | | | | | 290 | | | | | 295 |
| Phe | Arg | Pro | Phe | Val | Pro | Arg | Leu | Ala | Arg | Leu | Tyr | Pro | Asn | Met | Asn |
| | | | | 300 | | | | | 305 | | | | | 310 | |
| Leu | Glu | Leu | Gln | Gly | Ser | Val | Pro | Ser | Ala | Pro | Leu | Leu | Asn | Phe | Ser |
| | | | 315 | | | | | 320 | | | | | 325 | | |

-continued

| Pro | Gly | Asn<br>330 | Leu | Ser | Val | Asp | Pro<br>335 | Tyr | Met | Ile | Asp<br>340 | Ala | Phe | Val |
| --- | --- | --- | --- | --- | --- | --- | --- | --- | --- | --- | --- | --- | --- | --- |
| Leu | Leu<br>345 | Pro | Ser | Ser | Ser | Lys<br>350 | Glu | Pro | Val | Phe | Arg<br>355 | Leu | Ser | Val | Ala |
| Thr<br>360 | Asn | Val | Ser | Ala | Thr<br>365 | Leu | Thr | Phe | Asn | Thr<br>370 | Ser | Lys | Ile | Thr | Gly<br>375 |
| Phe | Leu | Lys | Pro | Gly<br>380 | Lys | Val | Lys | Val | Glu<br>385 | Leu | Lys | Glu | Ser | Lys<br>390 | Val |
| Gly | Leu | Phe | Asn<br>395 | Ala | Glu | Leu | Leu | Glu<br>400 | Ala | Leu | Leu | Asn | Tyr<br>405 | Tyr | Ile |
| Leu | Asn | Thr<br>410 | Phe | Tyr | Pro | Lys | Phe<br>415 | Asn | Asp | Lys | Leu | Ala<br>420 | Glu | Gly | Phe |
| Pro | Leu<br>425 | Pro | Leu | Leu | Lys | Arg<br>430 | Val | Gln | Leu | Tyr | Asp<br>435 | Leu | Gly | Leu | Gln |
| Ile<br>440 | His | Lys | Asp | Phe | Leu<br>445 | Phe | Leu | Gly | Ala | Asn<br>450 | Val | Gln | Tyr | Met | Arg<br>455 |
| Val |

( 2 ) INFORMATION FOR SEQ ID NO:3:

( i ) SEQUENCE CHARACTERISTICS:
        ( A ) LENGTH: 591 base pairs
        ( B ) TYPE: nucleic acid
        ( C ) STRANDEDNESS: single
        ( D ) TOPOLOGY: linear   ( i i ) MOLECULE TYPE: DNA     ( i x ) FEATURE:
        ( A ) NAME/KEY: CDS
        ( B ) LOCATION: 1..591

( i x ) FEATURE:
        ( A ) NAME/KEY: misc_feature
        ( D ) OTHER INFORMATION: "rLBP25"

( x i ) SEQUENCE DESCRIPTION: SEQ ID NO:3:

| GCC | AAC | CCC | GGC | TTG | GTC | GCC | AGG | ATC | ACC | GAC | AAG | GGA | CTG | CAG | TAT | 48 |
| --- | --- | --- | --- | --- | --- | --- | --- | --- | --- | --- | --- | --- | --- | --- | --- | --- |
| Ala<br>1 | Asn | Pro | Gly | Leu<br>5 | Val | Ala | Arg | Ile | Thr<br>10 | Asp | Lys | Gly | Leu | Gln<br>15 | Tyr | |
| GCG | GCC | CAG | GAG | GGG | CTA | TTG | GCT | CTG | CAG | AGT | GAG | CTG | CTC | AGG | ATC | 96 |
| Ala | Ala | Gln | Glu<br>20 | Gly | Leu | Leu | Ala | Leu<br>25 | Gln | Ser | Glu | Leu | Leu<br>30 | Arg | Ile | |
| ACG | CTG | CCT | GAC | TTC | ACC | GGG | GAC | TTG | AGG | ATC | CCC | CAC | GTC | GGC | CGT | 144 |
| Thr | Leu | Pro<br>35 | Asp | Phe | Thr | Gly | Asp<br>40 | Leu | Arg | Ile | Pro | His<br>45 | Val | Gly | Arg | |
| GGG | CGC | TAT | GAG | TTC | CAC | AGC | CTG | AAC | ATC | CAC | AGC | TGT | GAG | CTG | CTT | 192 |
| Gly | Arg<br>50 | Tyr | Glu | Phe | His | Ser<br>55 | Leu | Asn | Ile | His | Ser<br>60 | Cys | Glu | Leu | Leu | |
| CAC | TCT | GCG | CTG | AGG | CCT | GTC | CCT | GGC | CAG | GGC | CTG | AGT | CTC | AGC | ATC | 240 |
| His<br>65 | Ser | Ala | Leu | Arg | Pro<br>70 | Val | Pro | Gly | Gln | Gly<br>75 | Leu | Ser | Leu | Ser | Ile<br>80 | |
| TCC | GAC | TCC | TCC | ATC | CGG | GTC | CAG | GGC | AGG | TGG | AAG | GTG | CGC | AAG | TCA | 288 |
| Ser | Asp | Ser | Ser | Ile<br>85 | Arg | Val | Gln | Gly | Arg<br>90 | Trp | Lys | Val | Arg | Lys<br>95 | Ser | |
| TTC | TTC | AAA | CTA | CAG | GGC | TCC | TTT | GAT | GTC | AGT | GTC | AAG | GGC | ATC | AGC | 336 |
| Phe | Phe | Lys | Leu<br>100 | Gln | Gly | Ser | Phe | Asp<br>105 | Val | Ser | Val | Lys | Gly<br>110 | Ile | Ser | |
| ATT | TCG | GTC | AAC | CTC | CTG | TTG | GGC | AGC | GAG | TCC | TCC | GGG | AGG | CCC | ACA | 384 |
| Ile | Ser | Val<br>115 | Asn | Leu | Leu | Leu | Gly<br>120 | Ser | Glu | Ser | Ser | Gly<br>125 | Arg | Pro | Thr | |

-continued

```
GTT ACT GCC TCC AGC TGC AGC AGT GAC ATC GCT GAC GTG GAG GTG GAC       432
Val Thr Ala Ser Ser Cys Ser Ser Asp Ile Ala Asp Val Glu Val Asp
    130                 135                 140

ATG TCG GGA GAC TTG GGG TGG CTG TTG AAC CTC TTC CAC AAC CAG ATT       480
Met Ser Gly Asp Leu Gly Trp Leu Leu Asn Leu Phe His Asn Gln Ile
145                 150                 155                 160

GAG TCC AAG TTC CAG AAA GTA CTG GAG AGC AGG ATT TGC GAA ATG ATC       528
Glu Ser Lys Phe Gln Lys Val Leu Glu Ser Arg Ile Cys Glu Met Ile
                165                 170                 175

CAG AAA TCG GTG TCC TCC GAT CTA CAG CCT TAT CTC CAA ACT CTG CCA       576
Gln Lys Ser Val Ser Ser Asp Leu Gln Pro Tyr Leu Gln Thr Leu Pro
            180                 185                 190

GTT ACA ACA GAG ATT                                                    591
Val Thr Thr Glu Ile
            195
```

( 2 ) INFORMATION FOR SEQ ID NO:4:

( i ) SEQUENCE CHARACTERISTICS:
        ( A ) LENGTH: 197 amino acids
        ( B ) TYPE: amino acid
        ( D ) TOPOLOGY: linear     ( i i ) MOLECULE TYPE: protein     ( i x ) FEATURE:
        ( A ) NAME/KEY: misc_feature
        ( D ) OTHER INFORMATION: "rLBP25"

( x i ) SEQUENCE DESCRIPTION: SEQ ID NO:4:

```
Ala Asn Pro Gly Leu Val Ala Arg Ile Thr Asp Lys Gly Leu Gln Tyr
 1               5                  10                  15

Ala Ala Gln Glu Gly Leu Leu Ala Leu Gln Ser Glu Leu Leu Arg Ile
            20                  25                  30

Thr Leu Pro Asp Phe Thr Gly Asp Leu Arg Ile Pro His Val Gly Arg
        35                  40                  45

Gly Arg Tyr Glu Phe His Ser Leu Asn Ile His Ser Cys Glu Leu Leu
    50                  55                  60

His Ser Ala Leu Arg Pro Val Pro Gly Gln Gly Leu Ser Leu Ser Ile
65                  70                  75                  80

Ser Asp Ser Ser Ile Arg Val Gln Gly Arg Trp Lys Val Arg Lys Ser
                85                  90                  95

Phe Phe Lys Leu Gln Gly Ser Phe Asp Val Ser Val Lys Gly Ile Ser
                100                 105                 110

Ile Ser Val Asn Leu Leu Leu Gly Ser Glu Ser Ser Gly Arg Pro Thr
            115                 120                 125

Val Thr Ala Ser Ser Cys Ser Ser Asp Ile Ala Asp Val Glu Val Asp
    130                 135                 140

Met Ser Gly Asp Leu Gly Trp Leu Leu Asn Leu Phe His Asn Gln Ile
145                 150                 155                 160

Glu Ser Lys Phe Gln Lys Val Leu Glu Ser Arg Ile Cys Glu Met Ile
                165                 170                 175

Gln Lys Ser Val Ser Ser Asp Leu Gln Pro Tyr Leu Gln Thr Leu Pro
            180                 185                 190

Val Thr Thr Glu Ile
            195
```

METHOD FOR QUANTIFYING LIPOPOLYSACCHARIDE BINDING PROTEIN

BACKGROUND OF THE INVENTION

The present invention relates to methods for determination of the presence of Lipopolysaccharide binding protein (LBP) in body fluid samples including blood samples.

Lipopolysaccharide (LPS) is a common component of the outer membrane of Gram-negative bacteria and is responsible for many of the pathologic effects associated with gram-negative bacterial infection and endotoxemia. Because of the association between bacterial infection and sepsis, attempts have been made to correlate serum/plasma levels of endotoxin with disease. Typically, endotoxin levels have been measured using the Limulus amebocyte lysate (LAL) assay, in which endotoxin initiates a coagulation cascade that can be measured physically, turbidimetrically, or spectrophotometrically, Despite these attempts, however, no reliable correlations between endotoxin levels and sepsis severity or outcome have been identified. This is most likely due to the fact that (i) endotoxin levels in septic patients are very low (> 10 pg/L), several serum proteins interfere with the proteolytic LAL cascade, (iii) endotoxin, once in contact with blood, can be "detoxified" by interaction with a variety of blood components, including high-density lipoprotein (HDL) and low-density lipoprotein (LDL) and (iv) endotoxin from different gram-negative organisms varies in its ability to trigger the LAL cascade. Thus, the absolute levels of endotoxin in a patient sample may not correspond to the actual concentrations of bioactive endotoxin present in vivo.

Two proteins have been identified in humans and other animals that bind LPS with high affinity. These two proteins, Lipopolysaccharide binding protein (LBP), and bactericidal/permeability increasing protein (BPI) have roughly the same molecular weight and share 45% amino acid homology, yet exhibit distinct physiological differences. LBP is a 60 kD glycoprotein synthesized in the liver, while BPI is found in the azurophilic granules of neutrophils. LBP is found in the serum of normal humans at levels of 5–10 µg/mL but can reach levels of 50–100 µg/mL in septic patients. Schumann et al., Science, 249:1429 (1990) disclose the amino acid sequences and encoding cDNA of both human and rabbit LBP. Like BPI, LBP has a binding site for lipid A and binds to the LPS from rough (R-) and smooth (S-) form bacteria. Unlike BPI, LBP does not possess significant bactericidal activity. BPI has been observed to neutralize and inhibit the production of TNF resulting from interaction of LBP with LPS and CD14 on monocytes and macrophages. Marra et al., J. Immunol. 148:532 (1992), Weiss et al., J. Clin. Invest. 90:1122 (1992). In contrast, LBP is observed to enhance LPS-induced TNF production. Wright et al., Science, 249:1131 (1990). Thus, in contrast to BPI, LBP has been recognized as an immunostimulatory molecule. See, e.g., Seilhamer, PCT International Application WO 93/06228 which discloses a variant form of LBP which it terms LBP-β. Also of interest to the present invention are Ulevitch, PCT International Application WO 91/01639 which discloses, among other things, anti-LBP antibodies as an antisepsis therapeutic agent and U.S. Pat. No. 5,245,013 which relates to LBP and discloses antibodies which immunoreact with a polypeptide having homology to LBP.

LBP has been characterized in the art as an "acute phase protein", that is one of several plasma proteins such as C-reactive protein or serum amyloid A that increase in concentration in response to infectious and non-infectious tissue destructive processes. As such, it would be anticipated that LBP levels would be elevated in samples from patients suffering from a number of autoimmune diseases such as rheumatoid arthritis and lupus erythematosus. Of interest to the present invention are disclosures related to the assaying of BPI activity in subjects. von der Mohien et al., Abstract, 13th International Symposium on Intensive Care and Emergency Medicine, Brussels (March 1993) discloses the results of assays for serum levels of BPI in patients with gram-negative sepsis and healthy subjects. The abstract disclosed that no BPI was detectable under the conditions of the assay in the serum of healthy subjects while circulating BPI was detected in all septic patients. Also of interest is the disclosure of co-owned and copending U.S. patent application Ser. No. 08/175,276 filed Dec. 29, 1993 which is a continuation-in-part of application Ser. No. 08/125,677 filed Sep. 22, 1993 the disclosures of which are hereby incorporated by reference. Those patent applications disclose that levels of BPI in blood plasma samples correlate with the presence or absence of sepsis while levels of BPI in blood serum samples do not. The patent applications teach that levels of BPI present in serum are not representative of endogenous levels of BPI in circulating blood while levels of BPI in plasma are.

Also of interest to the present invention are the disclosures of Leturcq et al., Keystone Tahoe Endotoxin Conference, Mar. 1–7, 1992 (Abstract) in which the generation of monoclonal antibodies to human LBP is reported. Also reported is the screening of normal human serum samples for the presence of LBP. LBP levels for normal serum samples were reported to range from 1 µg/mL to 24 µg/mL with an average of 7 µg/mL. Further of interest is the disclosure of Richard Ulevitch at the American Society for Microbiology General Meeting in Atlanta, Ga. May 16–21 (1993) at which data was presented on LBP and soluble CD14 levels in the serum of septic and healthy individuals. The average soluble CD14 and LBP concentrations in the serum of healthy adults were 1 µg/mL and 7 µg/mL respectively. The average soluble CD14 and LBP concentrations in the serum of septic patients were reported to be 2 µg/mL and 55 µg/mL respectively.

Geller et al., Arch. Surg., 128:22–28 (1993) disclose experiments in which the induction of LBP mRNA was studied in three models known to induce acute phase responses: (1) LPS injection; (2) *Corynebacterium parvum* injection; and (3) turpentine injection. The publication reports that LBP mRNA is induced during hepatic inflammation and suggest that LBP is an acute-phase protein important in regulating the in vivo response to endotoxin.

Gallay et al., Infect. Immun., 61:378–383 (1993) disclose that an acute phase response in mice injected with silver nitrate induced LBP synthesis, and that LBP levels increase approximately 10-fold over normal levels after an acute-phase response.

There exists a desire in the art for methods for determining the exposure of subjects to endotoxin and for distinguishing the effects of exposure to endotoxin from other acute phase physiologic responses. Also desired are methods for diagnosing the presence or severity of gram-negative sepsis in a subject and for predicting the prognosis of a subject suffering from sepsis.

SUMMARY OF THE INVENTION

The present invention provides methods for determining exposure of a subject to endotoxin by assaying for LBP.

Specifically, the method comprises the steps of determining the concentration of LBP in a sample of body fluid from the subject and correlating the concentration of LBP with a standard indicative of the exposure to endotoxin. Such standards can include a subjective standard for a given subject determined by LBP levels of that subject in a pretreatment state such as prior to undergoing surgery. Exposure to endotoxin as a consequence of such surgery can be determined by comparing post-surgical LBP levels with the standard established prior to surgery for that subject. Where access to a pretreatment standard level of LBP is not available for a given individual a standard based upon population or subpopulation averages may be applied for comparison. Such an objective standard can be a concentration greater than approximately 15 µg/mL in human plasma or serum which represents the upper limit of the bottom quartile of subjects suffering from gram-negative sepsis. Subjects exhibiting LBP levels above that standard could presumptively be diagnosed as suffering from exposure to endotoxin while those having levels below that standard would not be. It is clear that alternative standards could be established depending upon the desired sensitivity and selectivity of an assay method and upon the subpopulation in which a given subject falls. For example, standards might be established at different levels for different ages, genders, ethnicities and underlying health conditions of various subpopulations. Moreover, it should be understood that standard levels will differ according to the identity of the particular body fluid which is assayed.

The invention further provides methods for diagnosing the presence or severity of sepsis in a subject comprising the steps of determining the concentration of LBP in a sample of body fluid from the subject and correlating the concentration of LBP with a standard indicative of the presence or severity of sepsis. The invention further provides methods for predicting the prognosis of a subject suffering from sepsis comprising the steps of determining the concentration of LBP in a sample of body fluid from the subject and correlating the concentration of LBP with a standard indicative of the prognosis of a subject suffering from sepsis.

DETAILED DESCRIPTION OF THE INVENTION

The present invention relates to methods for quantifying the presence of LBP in body fluids including blood. While the assay can be used to determine the presence and quantity of LBP which has been administered therapeutically, it is particularly useful for quantifying the presence of endogenous extracellular LBP in circulating blood as an indication of exposure of a subject to endotoxin. Moreover, quantifying the presence of LBP is contemplated to be useful in diagnostic and prognostic methods for evaluating gram-negative sepsis patients.

The present invention provides a sandwich ELISA assay for human LBP which exhibits high assay sensitivity, high specificity, and excellent reproducibility. As used herein "LBP" quantitated according to assay methods includes native LBP, recombinant LBP, LBP fragments and analogs as well as other LBP proteins and protein products.

The amino acid and nucleotide sequence of recombinant LBP are set out in co-owned and copending U.S. patent application Ser. No. 08/029,510 filed Jun. 17, 1993 as shown in SEQ ID NOS: 1 and 2 herein. A recombinant LBD amino-terminal fragment is characterized by the amino acid sequence of the first 197 amino acids of the amino-terminus of LBP as set out in SEQ ID NOS: 3 and 4 the production of which is described in co-owned and copending U.S. patent application Ser. No. 08/079,510 filed Jun. 12, 1993 the disclosure of which is incorporated herein. Such LBP protein products may be readily quantified in the subnanogram per mL range. The immunological assays are preferably carried out by enzyme linked immunosorbant (ELISA) sandwich assays but competitive assays and immunological assays utilizing other labelling formats may also be used. Preferred assays of the invention utilize anti-LBP antibodies, including monoclonal antibodies and affinity-purified rabbit polyclonal antibodies. Rabbit polyclonal anti-LBP antibodies may be prepared according to conventional methods using LBP as an immunogen.

Body fluids which can be assayed for the presence of LBP include whole blood with blood serum and blood plasma being preferred. Because LBP is a serum protein it is contemplated that it could be excreted and that analysis of LBP levels in urine may provide diagnostic and prognostic utility. The LBP immunoassays of the invention may also be used to determine the concentration of LBP in other body fluids including, but not limited to lung lavages, vitreous fluid, crevicular fluid, cerebralspinal fluid, saliva and synovial fluid.

Because LBP has been characterized as an "acute phase protein" it would be expected that LBP levels would be elevated in subjects suffering from autoimmune diseases. As one aspect of the present invention it has been found that LBP levels are not generally elevated over normal in subjects suffering from acute lymphoblastic leukemia (ALL), acute graft versus host disease (aGvHD), chronic lymphocytic leukemia (CLL), cutaneous T-cell lymphoma (CTCL), type 1 diabetes, aplastic anemia (AA), Crohn's Disease, psoriasis, rheumatoid arthritis (RA), scleroderma, and systemic lupus erythematosus (SLE).

Certain subjects tentatively identified as suffering from gram-negative sepsis but ultimately identified as suffering from gram-positive sepsis had elevated LBP levels. It is noted that translocation of bacteria and/or endotoxin from the gut into the bloodstream can occur in any infection. Thus, infections due to gram-positive bacteria or fungi may also lead to the presence of endotoxin or gram-negative bacteria in the blood and, therefore elevated levels of LBP.

The present invention is based in part upon the observation that serum and plasma levels of LBP directly correlate with a subject's exposure to biologically active LPS. Moreover, LBP levels appear to correlate with day 14 survival in that subjects with levels of circulating LBP below 27.3 µg/mL (the median value for 58 subjects suffering from gram-negative sepsis) tended to survive while those with levels of LBP above the median had higher mortality rates.

It is further contemplated by the invention that elevated levels of LBP may result from exposure to larger amounts of endotoxin, and may therefore be diagnostic of greater infection and/or endotoxemia severity. Elevated levels of LBP may also be used to indicate the suitability of using antibiotics directed against gram-negative bacteria or other therapeutic agents targeted directly to endotoxin such as BPI or anti-endotoxin antibodies including the monoclonal antibody E5.

Other aspects and advantages of the present invention will be understood upon consideration of the following illustrative examples. Example 1 relates to the preparation of affinity purified rabbit anti-BPI antibodies; Example 2 relates to the biotin labeling of such antibodies; and Example 3 relates to ELISA procedures utilizing such antibodies. Example 4 relates to the comparative immunoreactivity of rLBP, rLBP$_{25}$, rBPI AND rBPI$_{23}$. Example 5 relates to the measurement of rLBP spiked into pooled human plasma; and Example 6 relates to the comparison of LBP levels in human plasma and serum. Example 7 relates to the clinical correlations of endogenous LBP immunoreactivity with sepsis and other disease states in human plasma; and Example 8 relates to the effect of LPS administration on endogenous LBP levels in healthy subjects.

Example 1

PREPARATION OF AFFINITY PURIFIED RABBIT ANTI-rLBP ANTIBODY

According to this example affinity purified rabbit anti-rLBP antibody was prepared. Specifically, rLBP (20 mg) produced according to co-owned and copending U.S. patent application Ser. No. 08/079,510 filed Jun. 17, 1993, the disclosure of which is hereby incorporated by reference was coupled to 10 mL of cyanogen bromide-activated Sepharose 4B (Sigma Chemical Co., St Louis, Mo.) in 0.2M bicarbonate, pH 8.6, containing 0.5 NaCl. Approximately 94% of the rLBP was coupled to the resin. Pooled antisera (125 mL) from two rabbits, immunized initially with rLBP$_{25}$ produced according to the methods of U.S. patent application Ser. No. 08/079,510 filed Jun. 17, 1993 and thereafter with rLBP, were diluted with an equal volume of phosphate buffered saline, pH 7.2 (PBS). A portion (50 mL) of the diluted antisera was passed through the 10 mL rLBP-Sepharose column; the column was then washed with PBS and bound antibodies were eluted with 0.1M glycine, pH 2.5. Collected fractions were immediately neutralized with 1M phosphate buffer, pH 8.0. Peak fractions were identified by measuring absorbance at 280 nm according to the method of Harlow et al., Antibodies: A Laboratory Manual, Cold Springs Harbor Laboratory Press, New York, p. 312 (1988). After several sequential column cycles, the affinity purified rabbit anti-LBP antibody was dialyzed against PBS-azide pH 7.2.

Example 2

PREPARATION OF BIOTIN LABELED RABBIT ANTI-rLBP ANTIBODY

In this example twenty milligrams of affinity purified rabbit anti-rLBP antibody produced according to the method of Example 1 was incubated with 2 mg of biotinamidocaproate N-hydroxysuccinimide ester (Sigma Chemical Co., St. Louis, Mo.) in 11 mL of 0.1M sodium bicarbonate pH 8.3 for two hours at room temperature. Unconjugated biotin was removed and the alkaline buffer exchanged by fractionating the reaction mixture on a PD-10 column (Pharmacia Biotech Inc., Piscataway, N.J.) equilibrated with PBS containing 0.1% sodium azide.

Example 3

ELISA PROCEDURE

Fifty microliters of affinity purified rabbit anti-rLBP antibody (2 µg/mL in PBS) were incubated overnight at 2°–8° C. (or alternatively, 1 hour at 37° C.) in the wells of Immulon 2 (Dynatech Laboratories Inc., Chantilly, Va.) microtiter plates. The antibody solution was removed and 200 µL of 1% non-fat milk in PBS (blocking agent) was added to all wells. After blocking the plates for 1 hour at room temperature, the wells were washed 3 times with 300 µL of wash buffer (PBS/0.05 % Tween-20).

Standards, samples and controls were diluted in triplicate with PBS containing 1% bovine serum albumin, 0.05 % Tween 20 (PBS-BSA/Tween) and 10 units/mL of sodium heparin (Sigma Chemical Co., St. Louis, Mo.) in separate 96-well plates. rLBP or rLBP$_{25}$ standard solutions were prepared as serial two-fold dilutions from 100 to 0.012 ng/mL. Each replicate and dilution of the standards, samples and controls (50 µL) was transferred to the blocked microtiter plates and incubated for 1 hour at 37° C. After the primary incubation, the wells were washed 3 times with wash buffer. Biotin-labeled rabbit anti-LBP antibody was diluted 1/2000 in PBS-BSA/Tween and 50 µL was added to all wells. The plates were then incubated for 1 hour at 37° C. Subsequently, all wells were washed 3 times with wash buffer. Alkaline phosphatase-labeled streptavidin (Zymed Laboratories Inc., San Francisco, Calif.) was diluted 1/2000 in PBS-BSA/Tween and 50 µL was added to all wells. After incubation for 15 minutes at 37° C., all wells were washed 3 times with wash buffer and 3 times with deionized water and the chromogenic substrate p-nitrophenylphosphate (1 mg/mL in 10% diethanolamine buffer) was added in a volume of 50 µL to all wells. Color development was allowed to proceed for 1 hour at room temperature, after which 50 µL of 1N NaOH was added to stop the reaction. The absorbance at 405 nm was determined for all wells using a Vmax Plate Reader (Molecular Devices Corp., Menlo Park, Calif.).

The mean absorbance at 405 nm ($A_{405}$) for all samples and standards (in triplicate) were corrected for background by subtracting the mean $A_{405}$ of wells receiving only sample dilution buffer (no LBP) in the primary incubation step. A standard curve was then plotted as $A_{405}$ versus ng/mL of rLBP or rLBP$_{25}$. The linear range was selected, a linear regression analysis was performed and concentrations were determined for samples and controls by interpolation from the standard curve.

Example 4

COMPARATIVE IMMUNOREACTIVITY OF rLBP, rLBP$_{25}$, rBPI AND rBPI$_{23}$

Figure 1:
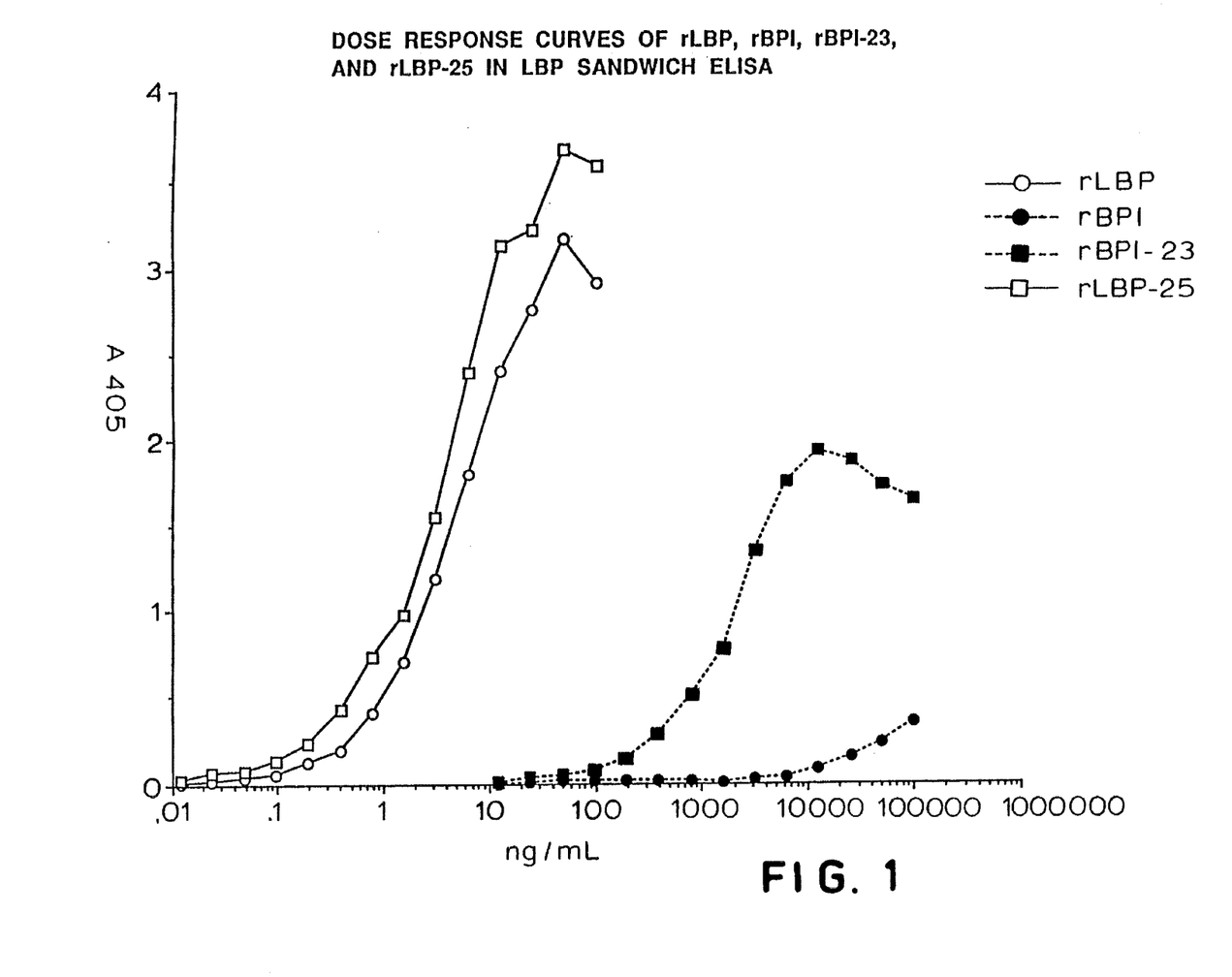
FIG. 1 depicts the dose-response curves for rLBP, rLBP$_{25}$, rBPI and rBPI$_{23}$ in LBP sandwich assays.

In this example, the immunoreactivity of rLBP, rLBP$_{25}$, rBPI and rBPI$_{23}$ were compared in the BPI sandwich ELISA to determine possible immunologic cross-reactivity. Despite considerable sequence homology between LBP and BPI (see, e.g., Schumann et al., Science, 249:1429 (1990), the results illustrated in FIG. 1 show that, on a mass basis, rBPI$_{23}$ produced a signal which was approximately 3 orders of magnitude lower than that of rLBP$_{25}$ and rLBP, while rBPI produced a signal that was approximately 5 orders of magnitude lower than that of rLBP and rLBP$_{25}$. For example, a concentration of 100,000 ng/mL (100 µg/mL) of rBPI or 400 ng/mL rBPI$_{23}$ generated a signal which was equal to that produced by 0.8 ng/mL of rLBP or 0.4 ng/mL of rLBP$_{25}$. These results demonstrate minimal cross-reactivity of the antibody with BPI and confirm the specificity of the assay for LBP.

Example 5

MEASUREMENT OF rLBP SPIKED INTO POOLED HUMAN PLASMA

In this example, the recovery of rLBP in human blood fluids was evaluated by examining pooled human plasma spiked with different concentrations of rLBP and then frozen and thawed prior to measurement in the sandwich ELISA. Recovery of spiked LBP was defined as the amount of LBP measured in spiked human plasma samples minus the concentration in the unspiked control, divided by the actual amount spiked in the sample. The fraction recovered was multiplied by 100 and the results were expressed as a percentage of the input concentration. Recovery of different concentrations of rLBP spiked into pooled human plasma samples averaged 68% and ranged from 59% at 42 µg/mL to 78% at 168 µg/mL. Table I summarizes the recovery data for each LBP spiked plasma sample.

TABLE I

Recovery of rLBP Spiked into Pooled Citrated Human Plasma

| Amount Spiked (µg/mL) | Amount Measured (µg/mL) | Amount Recovered (µg/mL) | Percent Recovery |
|---|---|---|---|
| 0 | 2.47 | — | — |
| 10.5 | 9.85 | 7.38 | 70% |
| 21 | 16.1 | 13.63 | 65% |
| 42 | 27.3 | 24.83 | 59% |
| 84 | 60.8 | 58.33 | 69% |
| 168 | 133 | 130.53 | 78% |
| | | Mean Recovery | 68% |

Example 6

COMPARISON OF PLASMA AND SERUM LBP LEVELS

According to this example concentrations of LBP in the serum and plasma of healthy subjects were assayed and compared utilizing the sandwich ELISA assay according to Example 3. Plasma concentrations of LBP were found to be essentially the same as serum concentrations for LBP when the plasma volume was corrected for dilution (dividing by a factor of 0.85) resulting from the addition of anticoagulant. Plasma concentrations in normal human subjects were found to be 3.1 µg/mL (S.D. 0.9 µg/mL) or 3.7 µg/mL (S.D. 1.1 µl/mL) corrected, compared with 3.7 µg/mL (S.D. 0.9 µg/mL) for serum.

Example 7

CLINICAL CORRELATIONS OF ENDOGENOUS LBP IMMUNOREACTIVITY IN HUMAN PLASMA

Figure 2A:
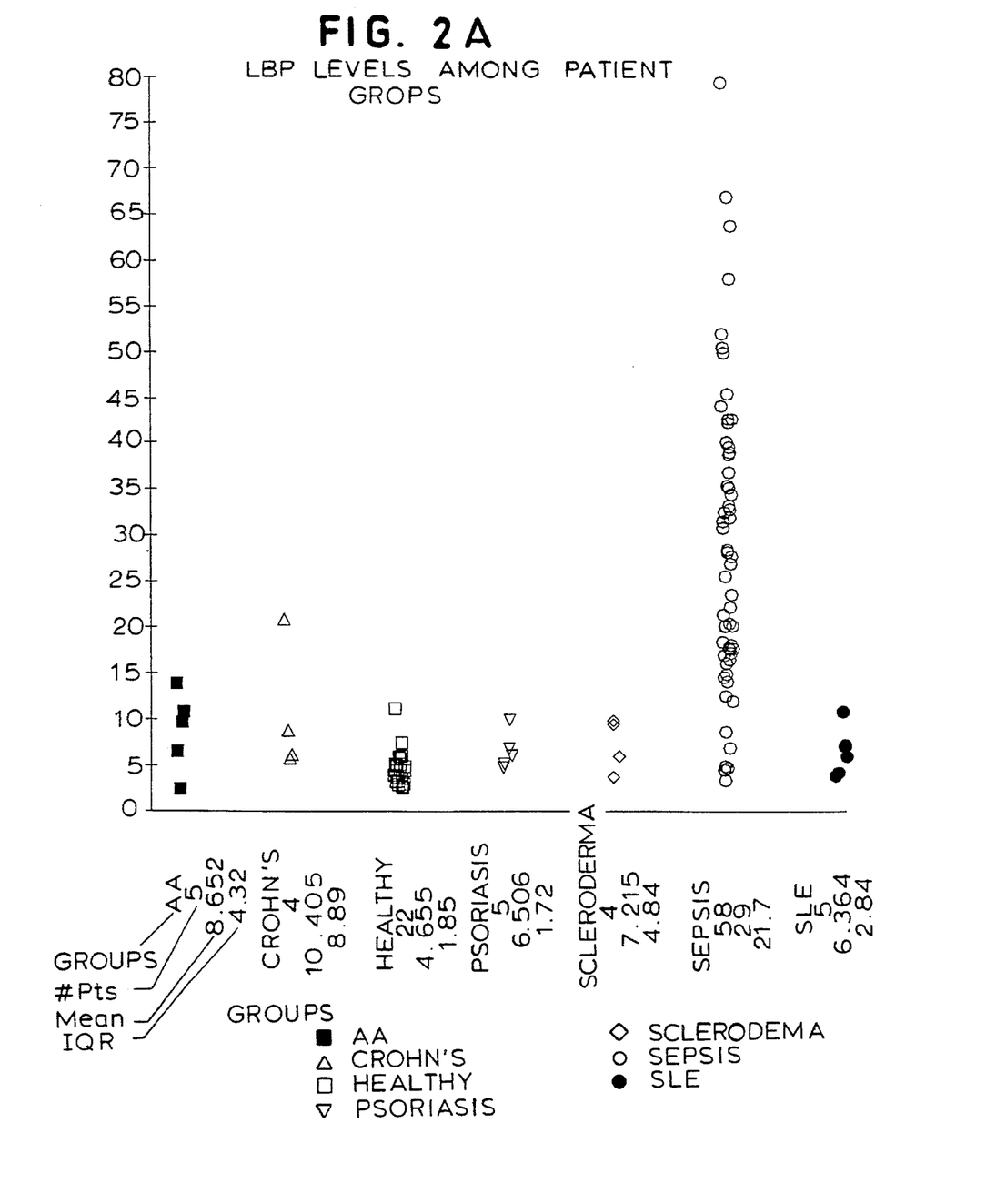
FIGS. 2a and 2b depict scattergrams of LBP levels in the plasma of healthy human subjects and human subjects suffering from various disease states.
Figure 2B:
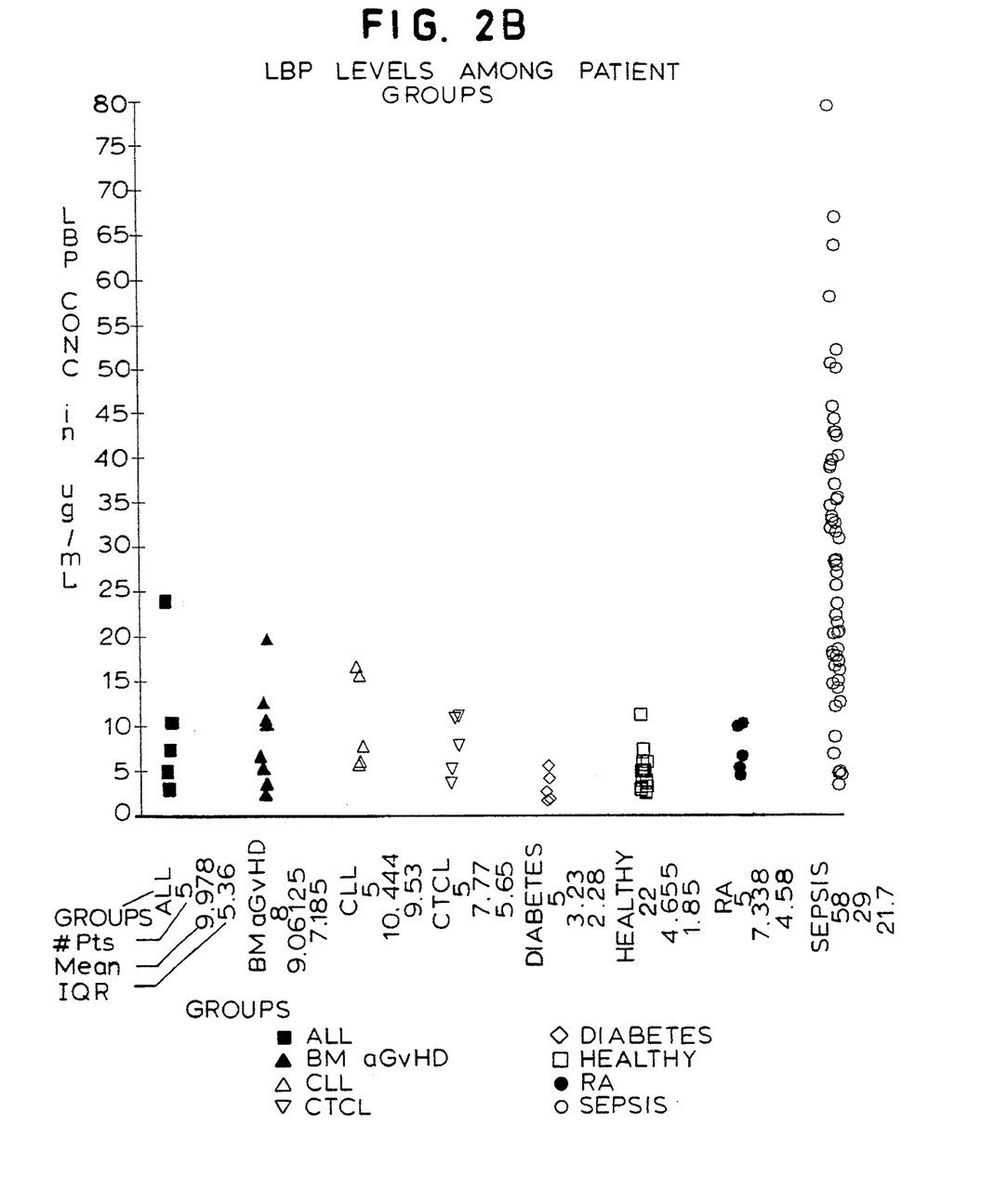

In this example endogenous LBP immunoreactivity was measured in human plasma and serum samples collected from a variety of subjects suffering from gram-negative sepsis and a variety of other clinical conditions. Specifically, plasma samples of healthy individuals (22 subjects) and individuals diagnosed with gram-negative sepsis (58 subjects) were assayed for LBP levels. Serum samples of individuals with acute lymphoblastic leukemia (ALL) (5 subjects); acute graft versus host disease (aGvHD) (8 subjects); chronic lymphocytic leukemia (CLL) (5 subjects); cutaneous T-cell lymphoma (CTCL) (5 subjects); type 1 diabetes (5 subjects); aplastic anemia (AA) (5 subjects); Crohn's Disease (4 subjects); psoriasis (5 subjects); rheumatoid arthritis (RA) (5 subjects); scleroderma (4 subjects), and systemic lupus erythematosus (SLE) (5 subjects) were assayed for LBP levels. The results are shown in FIG. 2a and 2b. While LBP levels among subjects diagnosed as suffering from gram-negative sepsis were elevated it was found that LBP levels are not elevated over normal in subjects suffering from acute lymphoblastic leukemia, acute graft versus host disease, chronic lymphocytic leukemia, cutaneous T-cell lymphoma, type 1 diabetes, aplastic anemia, Crohn's Disease, psoriasis, rheumatoid arthritis, scleroderma, and systemic lupus erythematosus (SLE). Accordingly, the LBP assay of the invention is valuable for distinguishing conditions associated with endotoxin from other acute phase conditions (such as RA, SLE and the like).

Example 8

THE EFFECT OF LPS ADMINISTRATION ON ENDOGENOUS LBP LEVELS IN HEALTHY SUBJECTS

Figure 3:
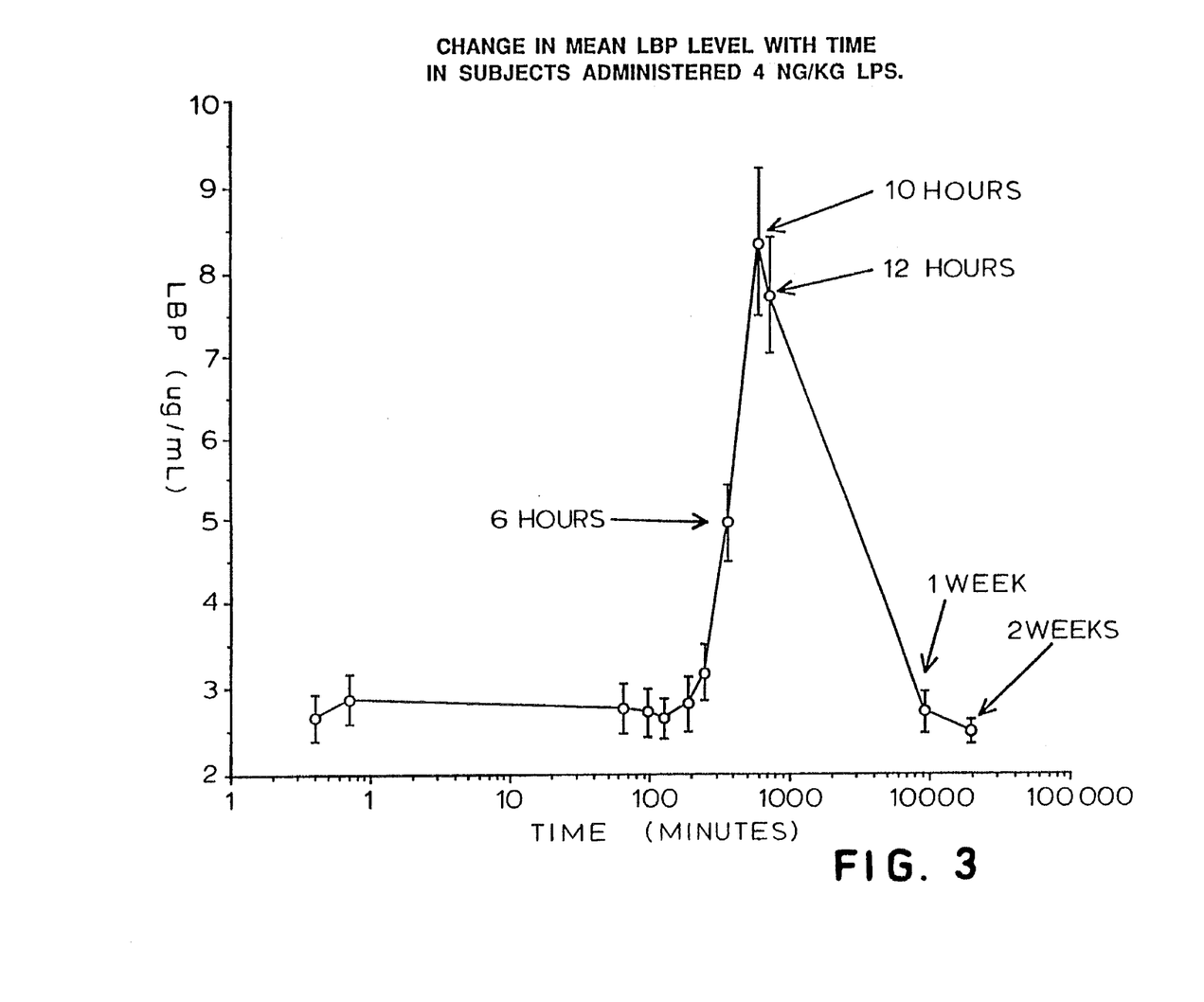
FIG. 3 depicts LBP levels in healthy subjects treated with LPS.

In this example, the effect of LPS administration on endogenous LBP immunoreactivity in healthy human subjects was determined. Specifically, healthy subjects were monitored utilizing the LBP sandwich assay for changes in LBP plasma levels at various time points after intravenous administration of 4 ng/kg LPS (16 subjects) or in control subjects (2) not receiving LPS. The results illustrated in FIG. 3 show the change in mean plasma LBP concentration with time. For those subjects treated with LPS LBP levels began to rise about 6 hours after LPS administration. Peak LBP plasma levels were observed in most subjects between 10 to 12 hours after the LPS administration. The average increase from baseline to peak LBP level was approximately 3-fold. Over this time period the mean LBP levels in control subjects remained within normal range (approximately 5 µg/mL).

It is contemplated that additional analysis will illustrate the correlation of LBP levels in body fluids with the symptoms of exposure to endotoxin and that LBP levels will be diagnostic and prognostic of disease states resulting from exposure to endotoxin.

It is contemplated that additional analysis will illustrate the correlation of LBP levels with symptoms of bacterial infections, endotoxemia and sepsis including conditions associated with sepsis including DIC and ARDS.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method for screening for gram-negative bacterial endotoxin involvement in an acute phase response in humans comprising:

(a) contacting a blood sample from a subject exhibiting an acute phase response with a specific binding partner for lipopolysaccharide binding protein, (b) determining the level of lipopolysaccharide binding protein in said blood sample, and (c) comparing the level of lipopolysaccharide binding protein determined in step (b) to levels of lipopolysaccharide binding protein in blood circulation in normal subjects, elevated levels of lipopolysaccharide binding protein being indicative of an acute phase response involving gram-negative bacterial endotoxin.

2. The method of claim 1 wherein the acute phase response is associated with sepsis.

* * * * *